(12) United States Patent
Strauss et al.

(10) Patent No.: US 10,930,370 B2
(45) Date of Patent: Feb. 23, 2021

(54) POLYNUCLEOTIDE SEQUENCER TUNED TO ARTIFICIAL POLYNUCLEOTIDES

(71) Applicant: Microsoft Technology Licensing, LLC, Redmond, WA (US)

(72) Inventors: Karin Strauss, Seattle, WA (US); Siena Dumas Ang, Seattle, WA (US); Luis Ceze, Seattle, WA (US); Yuan-Jyue Chen, Seattle, WA (US); Hsing-Yeh Parker, Woodinville, WA (US); Bichlien Nguyen, Seattle, WA (US); Robert Carlson, Seattle, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 944 days.

(21) Appl. No.: 15/607,364

(22) Filed: May 26, 2017

(65) Prior Publication Data

US 2018/0253528 A1 Sep. 6, 2018

Related U.S. Application Data

(60) Provisional application No. 62/467,055, filed on Mar. 3, 2017.

(51) Int. Cl.
| | |
|---|---|
| *G16B 30/00* | (2019.01) |
| *C12Q 1/6869* | (2018.01) |
| *G16B 30/20* | (2019.01) |
| *G16B 50/40* | (2019.01) |

(52) U.S. Cl.
CPC .......... *G16B 30/00* (2019.02); *C12Q 1/6869* (2013.01); *G16B 30/20* (2019.02); *G16B 50/40* (2019.02)

(58) Field of Classification Search
None
See application file for complete search history.

(56) References Cited

U.S. PATENT DOCUMENTS

| 8,404,828 B2 | 3/2013 | Kakol et al. |
| 8,889,348 B2 | 11/2014 | Ju |
| 9,150,918 B2 | 10/2015 | Turner et al. |
| 2015/0261664 A1 | 9/2015 | Goldman et al. |
| 2015/0275289 A1 | 10/2015 | Otwinowski et al. |
| 2015/0284769 A1 | 10/2015 | Schroeder |
| 2016/0110498 A1 | 4/2016 | Bruand et al. |
| 2016/0378916 A1 | 12/2016 | Drmanac et al. |
| 2018/0230509 A1 | 8/2018 | Chen et al. |

FOREIGN PATENT DOCUMENTS

| CN | 104850760 A | 8/2015 |
| CN | 105022935 A | 11/2015 |
| IN | 2406/CHE/2010 | 11/2012 |
| WO | WO2015057985 A1 | 4/2015 |
| WO | WO2016154540 A1 | 9/2016 |

OTHER PUBLICATIONS

Jain et al. The Oxford Nanopore MinION: delivery of nanopore sequencing to the genomics community Genome Biology vol. 17, article 239 (Year: 2016).*

Batu, et al., "Reconstructing Strings from Random Traces", In Proceedings of the Fifteenth Annual ACM-SIAM Symposium on Discrete Algorithms, Jan. 11, 2004 , pp. 910-918.

Blawat, et al., "Forward Error Correction for DNA Data Storage", In Proceedings of the International Conference on Computational Science, vol. 80, Published on: Jun. 6, 2016, pp. 1011-1022.

Bornholt, et al., "A DNA-based Archival Storage System", In Proceedings of the Twenty-First International Conference on Architectural Support for Programming Languages and Operating Systems, Published on: Apr. 2, 2016, pp. 637-649.

Carr, Katie, "Milenkovic Looks for Big Data Storage Solution in Dna Storage", https://www.ece.illinois.edu/newsroom/article/9755, Published on: Oct. 29, 2014, 4 pages.

Church, et al., "Next-Generation Digital Information Storage in DNA", In Journal of Science Express, Published on: Aug. 16, 2012, 2 pages.

"Expanding the Genetic Code with Synthetic Bases", epigenie, Jul. 27, 2015, Available at: http://epigenie.com/expanding-the-genetic-code-with-synthetic-bases/, 3 pages.

Erlich, et al., "Capacity-approaching DNA storage" and "Supplementary Information",bioRxiv, http://biorxiv.org/content/biorxiv/early/2016/09/09/074237.2.full.pdf, Sep. 9, 2016, 35 pages.

Erlich, et al., "DNA Fountain enables a robust and efficient storage architecture", In Journal of Science, vol. 355, Mar. 3, 2017, pp. 950-954.

Extance, Andy, "How DNA could store all the world's data", http://www.nature.com/news/how-dna-could-store-all-the-world-s-data-1.20496, Published on: Sep. 2, 2016, 9 pages.

Goela, et al., "Encoding Movies and Data in DNA Storage", https://web.archive.org/web/20160510211824/http:/ita.ucsd.edu/workshop/16/files/paper/paper_3187.pdf, Published on: May 10, 2016, 1 page.

Goldman, et al., "Towards practical, high-capacity, low-maintenance information storage in synthesized DNA", In Journal of Nature, vol. 494, Published on: Feb. 7, 2013, pp. 77-80.

(Continued)

*Primary Examiner* — John S Brusca
(74) *Attorney, Agent, or Firm* — Newport IP, LLC; Benjamin A. Keim

(57) ABSTRACT

Artificial polynucleotides may have different characteristics than natural polynucleotides so conventional base-calling algorithms may make incorrect base calls. However, because artificial polynucleotides are typically designed to have certain characteristics, the known characteristics of the artificial polynucleotide can be used to modify the base-calling algorithm. This disclosure describes polynucleotide sequencers adapted to sequence artificial polynucleotides by modifying a base-calling algorithm of the polynucleotide sequencer according to known characteristics of the artificial polynucleotides. The base-calling algorithm analyzes raw data generated by a polynucleotide sequencer and identifies which nucleotide base occupies a given position on a polynucleotide strand.

17 Claims, 6 Drawing Sheets

(56) References Cited

OTHER PUBLICATIONS

Grass, et al., "Robust Chemical Preservation of Digital Information on DNA in Silica with Error-Correcting Codes", In Proceedings of Angewandte Chemie International Edition, vol. 54, Issue 8, Published on: Feb. 16, 2015, pp. 2552-2555.
"IDC, Where in the World is Storage", http://www.idc.com/downloads/where_is_storage_infographic_243338.pdf, Retrieved on: Mar. 8, 2017, 1 page.
Kosuri, et al., "Large-scale de novo DNA synthesis: technologies and applications", In Journal of Nature Methods, vol. 11, Issue 5, May 2014, pp. 499-507.
Martineau, Kim, "Researchers Store Computer Operating System and Short Movie on DNA", http://datascience.columbia.edu/researchers-store-computer-operating-system-dna, Published on: Mar. 2, 2017, 2 pages.
Mitra, et al., "Strategies for Achieving High Sequencing Accuracy for Low Diversity Samples and Avoiding Sample Bleeding Using Illumina Platform", In Journal of Plos One, Apr. 10, 2015, pp. 1-21.
Schreiber, et al. "Analysis of Nanopore Data using Hidden Markov Models", UC Santa Cruz Previously Published Works, available at <<http://escholarship.org/uc/item/8341m6kv>>, Published Feb. 3, 2015, 9 pages.
Synthorx.com, "A paradigm shift in biology that can advance all industries", Retrieved on: Aug. 22, 2016, Available at: http://synthorx.com/applications/, 1 page.
Wilson, et al., "Sequence verification of synthetic DNA by assembly of sequencing reads", In Journal of Nucleic Acids Research, vol. 41, Issue 1, Oct. 4, 2012, pp. 1-11.
Xu, et al., "Design of 240,000 orthogonal 25mer DNA barcode probes", In Proceedings of the National Academy of Sciences, vol. 106, Issue 7, Feb. 17, 2009, pp. 2289-2294.
Yazdi, et al., "A Rewritable, Random-Access DNA-Based Storage System", In Journal of Scientific reports, vol. 5, May 2015, pp. 1-26.
Yazdi, et al., "DNA-Based Storage: Trends and Methods", In Journal of IEEE Transactions on Molecular, Biological and Multi-Scale Communications, vol. 1, Issue 3, Sep. 2015, 20 pages.
Yazdi, et al., "Portable and Error-Free DNA-Based Data Storage", bioRxiv, http://biorxiv.org/content/early/2016/10/05/079442, Published on: Jan. 2016, pp. 1-4.
Zadeh, et al., "Software News and Updates NUPACK: Analysis and Design of Nucleic Acid Systems", In Journal of Computational Chemistry, vol. 32, Jan. 2015, pp. 170-173.
"Non Final Office Action Issued in U.S. Appl. No. 15/431,897", dated Aug. 15, 2019, 14 pages.
Shendure, et al., "Next-Generation DNA Sequencing", In Journal of the Nature Biotechnology, vol. 26, Issue 10, Oct. 2008, pp. 1135-1145.
"Ex Parte Quayle Issued in U.S. Appl. No. 15/431,897", dated Jan. 3, 2020, 6 pages.

\* cited by examiner

POLYNUCLEOTIDE SEQUENCER TUNED TO ARTIFICIAL POLYNUCLEOTIDES

CROSS-REFERENCE TO RELATED APPLICATION

This application claims the benefit of U.S. Provisional Patent Application Ser. No. 62/467,055 filed on Mar. 3, 2017, entitled "Scaling Up DNA Data Storage and Random Access Retrieval," the entirety of which is expressly incorporated herein by reference.

BACKGROUND

Polynucleotide sequencers have been developed to read natural DNA. Strands of natural DNA have high diversity (i.e., individual strands are unlike each other) and are sheared randomly (i.e., strand length and the location of strand shearing is random). Accordingly, the hardware and software of polynucleotide sequencers are designed with certain assumptions about the polynucleotides they sequence. One assumption is that there is a uniform distribution of the four natural DNA nucleotides adenine (A), guanine (G), thymine (T), cytosine (C) or in the case of RNA the nucleotides A, G, C, and uracil (U). However, artificial polynucleotides may include highly conserved regions or other non-natural characteristics that make it difficult for current polynucleotide sequencers to properly calibrate and generate accurate sequence data. Artificial nucleotides may be sequenced without modification to polynucleotide sequencers and the results may be accepted as is. However, the sequencing data will then likely have errors because the molecule processed by the polynucleotide sequencer does not have the characteristics for which the polynucleotide sequencer is tuned. One previous solution is to modify the artificial polynucleotide strands to have a region with characteristics similar to natural DNA. This solution incurs overheads by requiring more bases to be included in the artificial polynucleotide strands and requiring additional steps to add these regions.

SUMMARY

This Summary is provided to introduce a selection of concepts in a simplified form that are further described below in the Detailed Description. This Summary is not intended to identify key features or essential features of the claimed subject matter nor is it intended to be used to limit the scope of the claimed subject matter.

Artificial polynucleotides that are synthesized have known sequences or at least some level of known structure and nucleotide base distribution because of the parameters used to perform the polynucleotide synthesis. Instead of adapting the molecules to the machines as done in previous approaches, the machines are adapted for the artificial polynucleotides. Specifically, knowledge about the artificial polynucleotides is used to modify how a polynucleotide sequencer interprets the raw data generated from sequencing polynucleotides. A base-calling algorithm can be modified based on the knowledge of the artificial polynucleotide in order to interpret the raw data in a way that is more accurate. Alternatively, a wholly new base-calling algorithm may be created.

In an implementation, an artificial polynucleotide strand having a distribution of nucleotides different than a natural polynucleotide and metadata describing the distribution of nucleotides in the artificial polynucleotide strand is received by a polynucleotide sequencer. A base-calling algorithm is modified based on the metadata to create a modified base-calling algorithm. Sequence data from the artificial polynucleotide strand is generated by the polynucleotide sequencer based on the modified base-calling algorithm.

In an implementation, a polynucleotide sequencer includes a sensor configured to generate a signal indicative of a nucleotide base associated with a sensed polynucleotide and an output device configured to render the sequence data in a human-readable form. Computer-readable media used by the polynucleotide sequencer includes instructions that, when executed by a processor, cause the processor to generate a custom base-calling algorithm based on a default base-calling algorithm and a known characteristic of the sensed polynucleotide. The instructions also cause the processor to create the sequence data based on the characteristics of the signal and the custom base-calling algorithm. The sequence data can be rendered on an output device in human-readable form.

In an implementation, sequencing data is corrected based on a known characteristic of a polynucleotide strand. Sequence data is generated for the polynucleotide strand according to a first base-calling algorithm. This sequence data is compared to the known characteristic of the polynucleotide strand. A difference is identified between the sequence data and the known characteristic. The base-calling algorithm is modified based on the difference to create a different base-calling algorithm. Sequence data for the polynucleotide strand is generated according to the different base-calling algorithm.

DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Figure 1:
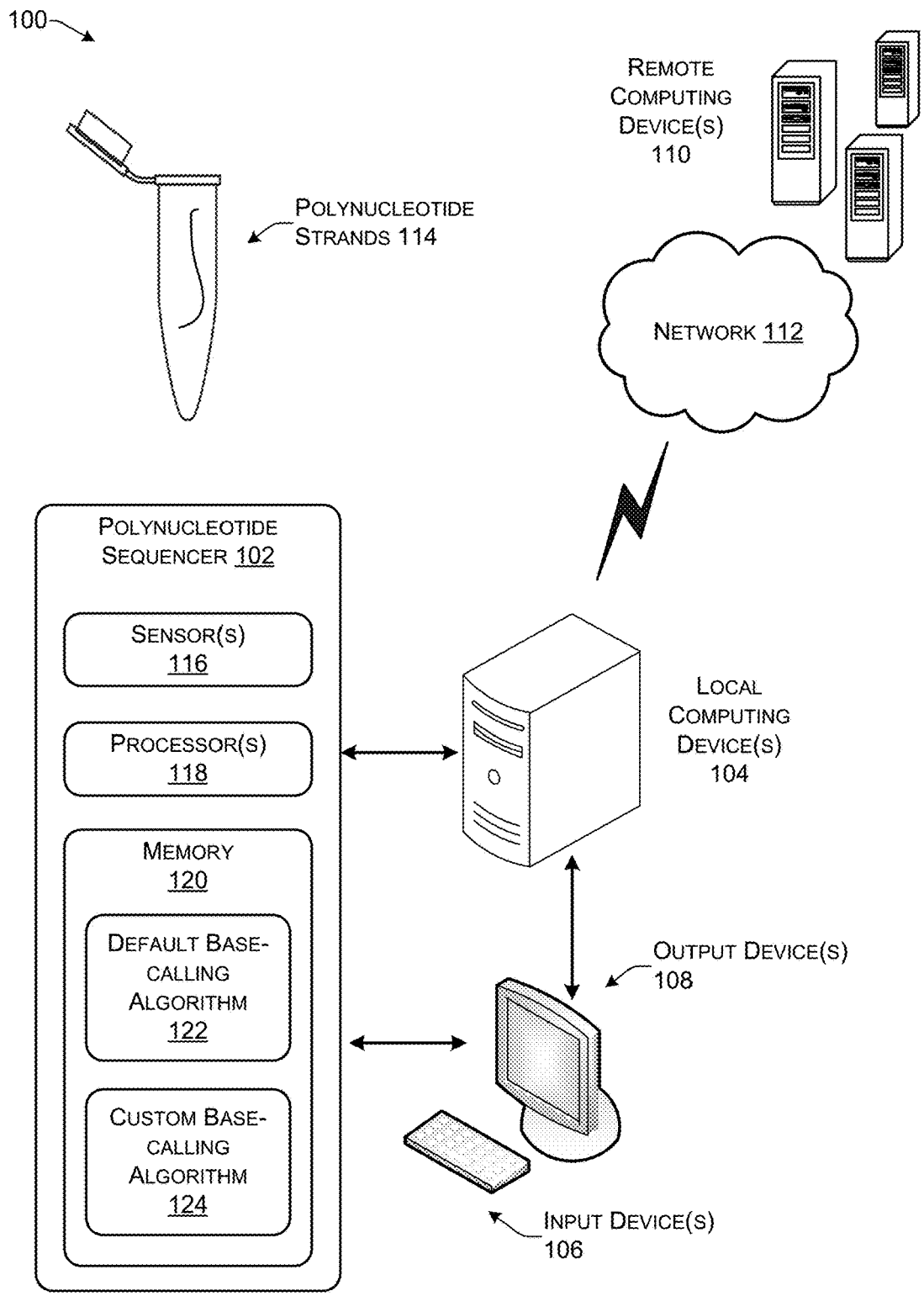
FIG. 1 shows a schematic representation of an illustrative polynucleotide sequencer.

This disclosure presents techniques for modifying polynucleotide sequencers to improve the sequencing of artificial polynucleotides. The modifications discussed in this disclosure relate to changes to a base-calling algorithm that account for differences between artificial polynucleotides and natural polynucleotides. Specific, known features of the artificial polynucleotides can be used to modify existing base-calling algorithms or to create new base-calling algorithms. The vast majority of polynucleotides sequenced come from natural sources and have characteristics of natural polynucleotides such as genomic DNA or messenger RNA (mRNA). Thus, the machines designed for automated sequencing of polynucleotides are designed to process natural polynucleotides. Artificial polynucleotides that have characteristics which differ from natural polynucleotides are difficult for conventional polynucleotide sequencers to sequence correctly. One solution is to modify the artificial polynucleotides to be similar to natural polynucleotides. Another solution is to modify some aspect of the hardware or software of the polynucleotide sequencer to accommodate artificial polynucleotides. This disclosure describes the latter solution, specifically software modifications that enable polynucleotide sequencers to sequence artificial polynucleotides more accurately than before.

Polynucleotide sequencers generally operate by loading the necessary reagents and polynucleotide samples to be sequenced into the machine and then starting the sequencing operation. One round of doing so is a sequencing run. Multiple different samples representing millions of different polynucleotide molecules can be sequenced simultaneously during a sequencing run. The individual polynucleotide molecules have intra-strand characteristics relating to a single strand's polymer sequence and a population of multiple polynucleotide strands in a single sequencing run has inter-strand characteristics relating to the similarities and differences between multiple ones of the polynucleotide strands. Because alterations to the software running the polynucleotide sequencers may be changed relatively easily compared to hardware changes, it is possible to alter the behavior of a polynucleotide sequencer for each sequencing run. Thus, the same machine can be used to sequence natural polynucleotides and different types of artificial polynucleotides.

"Polynucleotide" as used herein includes polymers of deoxyribose nucleic acids (DNA) or ribose nucleic acids (RNA) having the standard nucleotide bases A, G, T, and C for DNA or in the case of RNA A, G, C, and U, a subset of the standard nucleotide bases that uses less than four of the standard nucleotide bases, and unnatural bases such as 7-(2-thienyl)imidazo[4,5-b]pyridine (Ds), pyrrole-2-carbaldehyde (Pa), 2-amino-8-(2-thienyl)purine (s), f 2-amino-6-(N,N-dimethylamino)purine (x), pyridine-2-one (y), 3-nitropyrrole, 5-nitroindole, and 4-[3-(6-aminohexanamido)-1-propynyl]-2-nitropyrrole (Px) or other unnatural bases currently known or subsequently discovered. Examples provided in this disclosure may reference DNA or the nucleotide bases A, G, T, and C. However, this is to be understood as merely illustrative and does not exclude implementations using RNA, DNA-RNA hybrids, and/or unnatural bases.

"Artificial polymer" as used herein include artificial biological polymers and nonnatural polymers. Biological polymers include DNA, RNA, amino acids strands, and carbohydrate polymers. Nonnatural polymers include sequence-controlled polymers that are artificially synthesized from monomers other than biological molecules. Various types of nonnatural sequence-controlled polymers and methods for making such polymers having specific monomer sequences are known to those of ordinary skill in the art. Examples of nonnatural sequence-controlled polymers include polystyrene chains that incorporates single N-substituted maleimide units ((N-propyl maleimide, N-benzyl maleimide, N-methyl maleimide, and N-[3,5-bis(trifluoromethyl)phenyl]maleimide) and polyesters including two different lactone monomers.

FIG. 1 shows a schematic diagram of a polynucleotide sequencer system 100. The polynucleotide sequencer system 100 can include any known or later developed type of polynucleotide sequencer 102. Polynucleotide sequencers 102 include DNA sequencers and RNA sequencers. Examples of DNA sequencers include those that operate on the principal of sequencing-by-synthesis such as various models available from Illumina®, those that use nanopores to generate sequence data such as products available from Oxford Nanopore Technologies™, those that detect release of ions upon addition of a dNTP such as the Ion Torrent™ products available from Thermo Fisher Scientific™, those that use pyrosequencing such as the GeneReader™ NGS System from Qiagen®, those that use SOLID® sequencing such as the 5500 series SOLiD™ sequencers from Life Technologies™, those that use SMRT™ Sequencing such as the Sequel System available from PacBio®, as well as sequencers that use traditional Sanger sequencing such as the Genetic Analyzer available from Applied Biosystems™. RNA sequencing can be performed by creating complementary DNA (cDNA) from an RNA sample then sequencing the cDNA on a DNA sequencer. RNA sequencing may also be done by direct RNA sequencing which does not convert the RNA to DNA. Examples of direct RNA sequencing include nanopore devices available from Oxford Nanopore Technologies™ and DRS™ provided by SeqLL.

The polynucleotide sequencer 102 may be in communicative contact with one or more local computing device(s) 104. The local computing device(s) 104 may be implemented as a desktop computer, a notebook computer, a tablet computer, a smart phone, or the like. In an implementation, the local computing device(s) 104 may be in whole or part integrated into the polynucleotide sequencer 102 such as, for example, being included in the same housing as other components of the polynucleotide sequencer 102. The polynucleotide sequencer system 100 can also include one or more input devices 106 and one or more output devices 108. The input devices(s) 106 can include a keyboard, a pointing device, a touchscreen, a microphone, a camera, and the like. The output device(s) 108 can include a display, a speaker, a printer, or any other device configured to render data in human-readable form. The input device(s) 106 and the output device(s) 108 may be communicatively connected to the local computing device(s) 104 and/or to the polynucleotide sequencer 102.

The polynucleotide sequencing system 100 can also include remote components. The local computing device(s) 104 can be connected to one or more remote computing device(s) 110 via a network 112. The network 112 can include any type of communications network, such as a local area network, a wide area network, a mesh network, an ad hoc network, a peer-to-peer network, the Internet, a cable network, a telephone network, a wired network, a wireless network, combinations thereof, and the like. In an implementation, the remote computing device(s) 110 may be referred to as "cloud computing" resources, network servers, and the like.

One or more polynucleotide strands 114 are provided to the polynucleotide sequencer 102 for sequencing. In various implementations, the polynucleotide strands 114 can be artificial polynucleotides that have characteristics different from natural polynucleotides, artificial polynucleotides that have characteristics similar to natural polynucleotides, or natural polynucleotides. Techniques for preparing polynucleotide strands 114 for sequencing are well known to those of ordinary skill in the art and depend on the specific sequencing technology to be used. Some illustrative techniques are discussed in Green, M. and Sambrook, J., *Molecular Cloning: A Laboratory Manual*, Fourth Edition, Cold Spring Harbor Laboratory Press, Cold Spring Harbor (2012), Ch. 11 DNA Sequencing. The polynucleotide strands 114 can be prepared according to the specific protocol for the sequencing technology implemented by the polynucleotide sequencer 102. The polynucleotide strands 114 may be prepared by a protocol provided by a manufacture or seller of the polynucleotide sequencer 102.

The polynucleotide sequencer 102 includes one or more sensor(s) 116 that are configured to generate responses based on individual nucleotides in the polynucleotide strands 114. The specific type of sensor(s) 116 will vary with the sequencing technology. For example, with sequencing-by-synthesis, the sensors may include a camera such as a charge coupled device (CCD) camera that captures images of fluorescently labeled nucleotides excited by a laser. As a further example, a polynucleotide sequencer 102 that uses nanopore sequencing can include electrical signals generated by passing a potential across electrically insulative material containing a nanopore. Nanopore sequencing may function by using an electrically resistant membrane with a nanopore as the sensor(s) 116 that generates electrical current as a polynucleotide strand 114 passes through. As the polynucleotide strand 114 strand emerges from the nanopore, a portion of the polynucleotide strand 114 completes a temporary electrical circuit between the nanopore (first electrode) and a second electrode. The electrical circuit utilizes the electron tunneling current mediated by specific hydrogen-bonding molecular recognition events between portions of the polynucleotide strand 114 and the two electrodes. Polynucleotide sequencers 102 that detect ions emitted from synthesis of a growing polynucleotide use integrated circuits, complementary metal-oxide semiconductors (CMOS), and ion-sensitive field-effect transistors (ISFET) to detect a change in pH with the CMOS sensor. The signals generated by the sensor(s) 116 prior to subsequent processing are referred to in this disclosure as "raw data." Raw data does not itself indicate a particular base call, but through analysis can be interpreted as indicating which base call has the highest probability for a given position on one of the polynucleotide strands 114.

The polynucleotide sequencer system 100 can also include one or more processor(s) 118 located in any or all of the polynucleotide sequencer 102, the local computing device(s) 104, and the remote computing device(s) 110. The processor(s) 118 may be implemented as any suitable type of hardware processor such as a single core processor, a multicore processor, a central processing unit (CPU), a graphical processing unit (GPU), application-specific integrated circuits (ASICs), programmable circuits such as Field Programmable Gate Arrays (FPGA), or the like. In one implementation, processor(s) 118 can use Single Instruction Multiple Data (SIMD) parallel architecture. For example, the processor(s) 118 can include one or more GPUs that implement SIMD. In some implementations, one or more of the processor(s) 118 can be implemented in software and/or firmware in addition to hardware implementations. Software or firmware implementations of the processor(s) 118 can include computer- or machine-executable instructions written in any suitable programming language to perform the various functions described. Software implementations of the processor(s) 118 may be stored in whole or part in a memory 120.

Alternatively, or additionally, the functionality of polynucleotide sequencing system 100 can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc.

The memory 120 may include removable storage, non-removable storage, local storage, and/or remote storage to provide storage of computer readable instructions, data structures, program modules, and other data. The memory 120 may be located in whole or in part on any of the polynucleotide sequencer 102, the local computing device(s) 104, and the remote computing device(s) 110. The memory 120 may be implemented as computer-readable media. Computer-readable media includes, at least two types of media, namely computer-readable storage media and communications media. Computer-readable storage media includes volatile and non-volatile, removable and non-removable media implemented in any method or technology for storage of information such as computer-readable instructions, data structures, program modules, or other data. Computer-readable storage media includes, but is not limited to, RAM, ROM, EEPROM, flash memory, solid-state storage, or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing device.

In contrast, communications media may embody computer readable instructions, data structures, program modules, or other data in a modulated data signal, such as a carrier wave, or other transmission mechanism. As defined herein, computer-readable storage media and communications media are mutually exclusive.

The memory 120 can include multiple modules that may be implemented as instructions stored in the memory 120 for execution by processor(s) 118 and/or implemented, in whole or in part, by one or more hardware logic components or firmware. The memory 120 can be used to store any number of functional components that are executable by the one or more processor(s) 118. In one implementation, these functional components comprise instructions or programs that are executable by the processor(s) 118 and that, when executed, implement operational logic for performing the operations attributed to the polynucleotide sequencer 102.

The memory 102 can include a module that provides a default base-calling algorithm 122. The default base-calling algorithm 122 may be any conventional base-calling algorithm. Persons of ordinary skill in the art will be aware of various conventional base-calling algorithms. For example, sequencing-by-synthesis can use base-calling algorithms such as Illumina's Bustard, Alta-Cyclic (Erlich, Y. et al., (2008) *Alta-Cyclic: A self-optimizing base caller for next-generation sequencing*. Nature Methods 5:679-682), probabilistic base calling (Rougemont, J., et al., (2008) *Probabilistic base calling of Solexa sequencing data*. BMC Bioinformatics 9: Article 431), BayesCall (Kao, W.-C., et al., (2009) *BayesCall: A model-based base-calling algorithm for high-throughput short-read sequencing*. Genome Research 19:1884-1895; also describing the Bustard algorithm), Swift (Whiteford, N., et al., (2009) *Swift: Primary data analysis for the Illumina Solexa sequencing platform*. Bioinformatics 25:2194-2199), or Ibis (Kircher, M., et al., (2009) *Improved base calling for the Illumina Genome Analyzer using machine learning strategies*. Genome Biol. 10(8): Article R83).

At a basic level, Bustard, for example, operates by converting fluorescence signals into actual sequence data with quality scores through taking intensities of four channels of light for every cluster in each cycle, determining concentrations of each base, and renormalizing concentrations by multiplying by ratio of average concentrations in a first cycle and a current cycle. It then uses a Markov model to determine transition matrix modeling probability of phasing (no new base synthesized), pre-phasing (two new bases synthesized), and normal incorporation. Phasing is the rate at which single molecules within a cluster lose sync with each other. Phasing is falling behind, pre-phasing is going ahead, and together they describe how well the chemistry is performing. Phasing and pre-phasing can be estimated over the first 12 cycles of each read and then applied to all subsequent cycles. Empirical phasing correction can also be used; it optimizes the phasing correction at every cycle by trying a range of corrections and selecting the one which results in the highest chastity (i.e., signal purity). A Markov model is a stochastic model used to model randomly changing systems where it is assumed that future states depend only on the current state not on the events that occurred before it (that is, it assumes the Markov property). Generally, this assumption enables reasoning and computation with the model that would otherwise be intractable. Finally, Bustard uses a transition matrix and observed concentrations of each base to determine concentrations in absence of phasing and reports these as base calls. This assumes that the crosstalk matrix is constant (cycle independent) for a given sequencing run.

Nanopore sequencing uses different base-calling algorithms which are also known to persons of ordinary skill in the art and include Oxford Nanopore Technologies' proprietary and cloud-based Metrichor which uses a hidden Markov model (HMM) where the hidden state corresponds to the DNA context present in the nanopore, and where the pore models are used to compute emission probabilities. The context is k=6 consecutive bases and the context typically shifts by one base in each step. An alternative open source base caller, Nanocall, also uses HMM and is described in David, M., et al., *Nanocall: an open source basecaller for Oxford Nanopore sequencing data*. Bioinformatics 2017; 33 (1): 49-55. An HMM is a statistical Markov model in which the system being modeled is assumed to be a Markov process with unobserved (hidden) states. An HMM can be presented as the simplest dynamic Bayesian network. In a hidden Markov model, the state is not directly visible, but the output, dependent on the state, is visible. DeepNano is an alternative base caller that uses a deep recurrent neural network rather than an HMM. See Boža, V., et al., *DeepNano: Deep Recurrent Neural Networks for Base Calling in MinION Nanopore Reads*. (2016). BasecRAWller is another base caller for nanpore sequencers that also uses recurrent neural networks (RNN) described in Stoiber, M. and Brown, J., *BasecRAWller: Streaming Nanopore Basecalling Directly from Raw Signal*. (2017) available at biorxiv.org/content/early/2017/05/01/133058. A recurrent neural network is a class of artificial neural network where connections between units form a directed cycle. This creates an internal state of the network which allows it to exhibit dynamic temporal behavior. Unlike feedforward neural networks, RNNs can use their internal memory to process arbitrary sequences of inputs. This basic architecture is a network of neuron-like units, each with a directed connection to every other unit. Each unit has a time-varying real-valued activation. Each connection has a modifiable real-valued weight. Some of the nodes are called input nodes, some output nodes, the rest hidden nodes.

The memory 102 can include a module that provides a custom base-calling algorithm 124. The custom base-calling algorithm 124 may be a modification of a default base-calling algorithm 122 or a new base-calling algorithm designed without reference to existing algorithms. The modification may include modifying the code of the module that provides the default base-calling algorithm 122. The modification can also include adding additional code that operates in place of default code. In one implementation, modification can include receiving indications of parameters from a user (e.g., there are five different types of bases, the GC % is less than 10%, etc.) that are then accounted for by the modified base-calling algorithm 124. For example, some base-calling algorithms use training as part of creating the model which makes base calls. If the polynucleotide strands 114 all have a known sequence (e.g., a sequence specifically added to serve as a primer binding site) then the "answer" for the correct base calls of that portion of any of the polynucleotide strands 114 is known. Thus, the base-calling algorithm can be trained to correctly call the known bases and that training will improve accuracy for base calling of the unknown bases. Some base-calling algorithms use transition probabilities to identify a most probable base call. The base-calling algorithm can be modified to account for the limited possibilities for a next base in a sequence when, for example the polynucleotide strand 114 is known to be free from homopolymer repeats, is known to lack a particular nucleotide base, etc. The modification will restrict the possible transitions that could be considered thereby increasing the probability of an accurate base call. Additionally, knowledge about the polynucleotide strands 114 may indicate that particular portions of the molecules are more suited for use in calibration of the polynucleotide sequencer 102 than other portions. The custom base-calling algorithm 124 can use the optimal portion of raw data from the polynucleotide strands 114 for calibration. Each of the modifications described above, as well as others not explicitly mentioned, may be combined to create a custom base-calling algorithm 124 that differs from the default base-calling algorithm 122.

Figure 2:
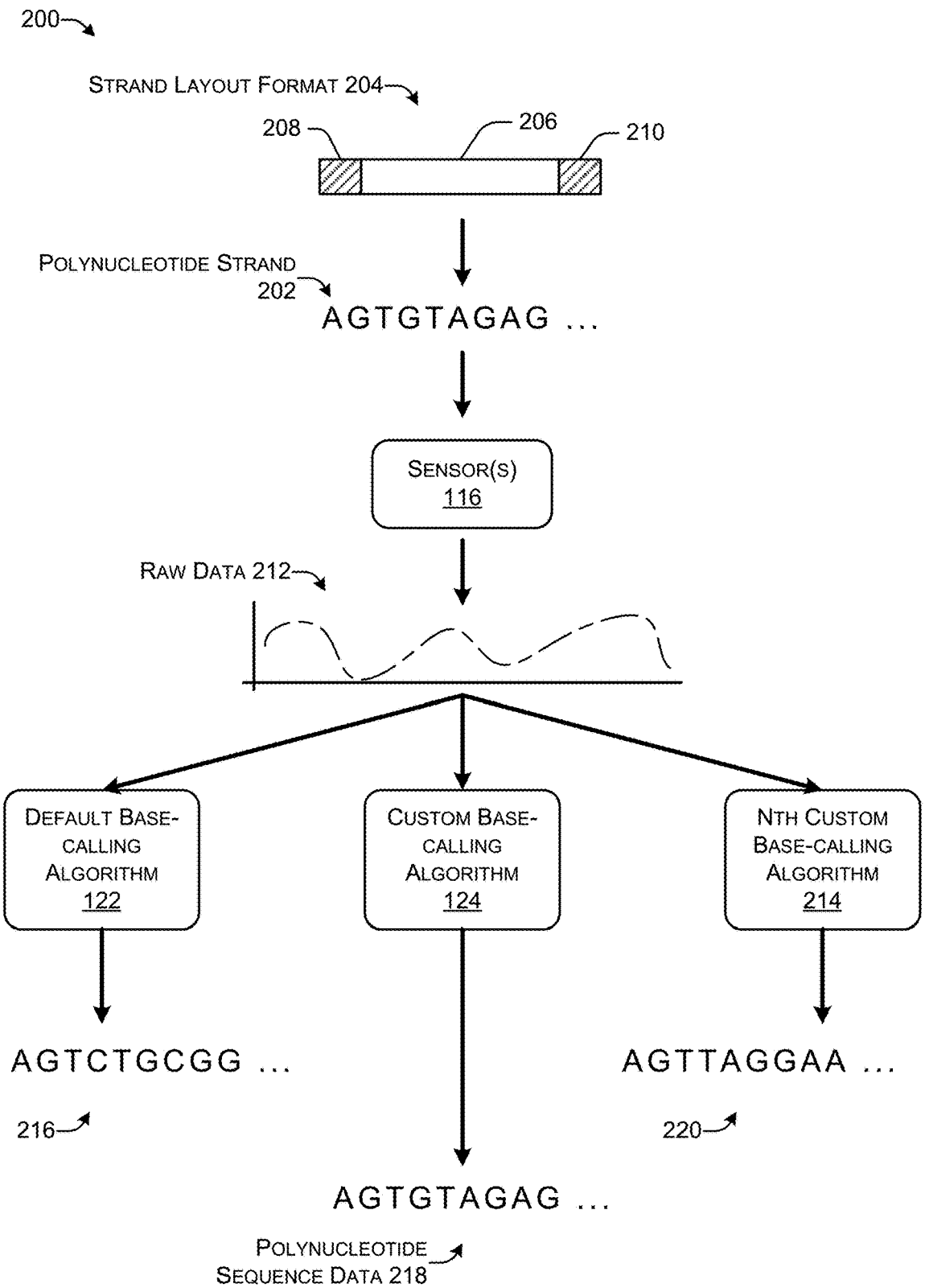
FIG. 2 shows application of base-calling algorithms to raw data generated by a polynucleotide sequencer.

FIG. 2 shows a schematic process 200 of generating polynucleotide sequence data from a polynucleotide strand 202. The polynucleotide strand 202 may be synthesized so that it has a strand layout format 204 which can include two or more separate regions. The strand layout format 204 may specify the length of each region and one or more features of that region. The details of the strand layout format 204 may be provided to a polynucleotide sequencer as data that is associated with a given set of polynucleotide strands 202. For example, a strand layout format 204 may be provided as electronic metadata that is provided to a polynucleotide sequencer as part of a sequencing run.

In the non-limiting example shown in FIG. 2, the strand layout format 204 specifies three regions: a middle region 206, a 5'-end region 208, and a 3'-end region 210. The 5'-end region 208 and the 3'-end region 210 may be primer binding sites. A length of the middle region 206 may be specified as a fixed nucleotide length (e.g., 100 nt) or as a range of possible lengths (e.g., 90-100 nt, 100+/−5 nt, 100+/−7% nt). A length of the 5'-end region 208 and the 3'-end region 210 may be the length of a polymerase chain reaction (PCR) primer (e.g., between about 8-30, 15-25, or 18-22 nt). The 5'-end region 208 and the 3'-end region 210 may have the same or different sequences. In some implementations, such as but not limited to primer binding sites, the sequence of the 5'-end region 208 and/or the 3'-end region 210 may be known and may be consistent throughout a population of polynucleotides including the polynucleotide strand 202. The knowledge that every polynucleotide in a sequencing run will have the same bases at the start and/or end of the molecule can be used to modify the base-calling algorithm.

For example, base-calling algorithms that use an iterative process may be forced to iterate over the region of the polynucleotide strand 202 that has a known sequence until the base calling-algorithm correctly identifies that sequence. This creates a base-calling algorithm that is itself generated based on data for which the answers are known, and thus, it is more likely to generate a correct answer for the base calls of other regions of the polynucleotide strand 202 in which the sequence is not known.

Different regions in a strand layout format 204 may have other characteristics that can be used to modify a base-calling algorithm. For example, the 5'-end region 208 and the 3'-end region 210 may have different distributions of nucleotide bases than the middle region 206. For example, the 5'-end region 208 may have a GC content of more than about 60%, 70%, 80%, or 90%. As a further example, the 3'-end region 210 may use fewer than all natural nucleotides such as omitting any one of A, G, C, or T. The middle region 206 may, for example, have a distribution of nucleotide bases that is similar to a natural polynucleotide such as about 25% each of A, G, C, and T.

There may also be different rules about the order of the nucleotides and these rules may vary with region of the strand layout format 204. For example, the polynucleotide strand 202 may be synthesized without homopolymer repeats in one or more regions. The length of permitted homopolymer repeats may be limited such as a maximum of 1, 2, 3, 4, 5, etc. repeating nucleotides in a single homopolymer repeat. Additionally, the number instances of homopolymer repeats within a polynucleotide strand may be limited such as only 1, 2, 3, 4, etc. instances of a homopolymer repeat per strand. One or more regions of the strand layout formation 204 may be synthesized according to other rules such as C not following T, homopolymer repeats only for A, etc. Identify Identity of any unnatural nucleotide bases included in the polynucleotide strand may also be included in the rules. Knowledge of these characteristics of the polynucleotide strand 202 and how those characteristics correlate with specific regions of a strand layout format 204 can be used to modify a base-calling algorithm.

In one implementation, the polynucleotide strand 202 may be synthesized to contain digital data. The digital data can be encoded in the polynucleotide strand 202 according to an encoding scheme which correlates the order of bases in the polynucleotide strand 202 with a binary sequence of 1s and 0s. Thus, the polynucleotide strand 202 can be synthesized to have a specific sequence that stores digital data which is ultimately processed by a computing device. The digital data stored in the polynucleotide strand 202 can include any type of digital data that may be stored in a conventional computer memory such as digital data related to at least one of audio content, video content, image content, or text content. U.S. Provisional Patent Application Ser. No. 62/467,055 describes, for example, a file encoded by 10,000 oligonucleotides.

The digital data may be referred to as a "payload" and this payload may be placed in the middle region 206 according to the strand layout format 204. The digital data that makes up a single file such as, for example a video file, may need to be stored on multiple different polynucleotide strands 202 due to the volume of data and the data storage limitations of any single polynucleotide strand 202. File identifiers can be used to reassemble the group of bit strings back into the digital data after decoding of a group of payloads from multiple polynucleotide strands 202. The file identifiers can individually be sequences of nucleotides that are the same for a particular file and can be stored in one of the 5'-end region 208 or the 3'-end region 210. To illustrate, the digital data can be stored in the middle region 206 and a file identifier for the payload can be included in the 5'-end region 208. The file identifier may also function as a primer binding site.

Additionally, the polynucleotide strand 202 can include nucleotides that represent information in addition to the file identifier. For example, the polynucleotide strand 202 can include one or more nucleotides that indicate ordering information. The ordering information can indicate a location within the digital data for each bit string of the group of bit strings encoded by a particular payload. Thus, in some implementations, file identifiers and ordering information can be used to reproduce the original bit string of the digital data from a large number of polynucleotide strands including the polynucleotides strand 202. The encoding scheme that correlates the nucleotide sequence of the polynucleotide strand 202 with binary data may impose specific and known limitations on the order of the nucleotides. Thus, if the middle region 206 is known to contain payload information encoded according to an encoding scheme, then characteristics about the sequence in the middle region 206 will be known due to the rules that govern the synthesis of the entire population of polynucleotide strands including polynucleotide strand 202. This is true even if the specific sequence of all or part of polynucleotide strand 202 is not known. These characteristics can describe the frequency with which individual ones of the natural nucleotides or unnatural nucleotides are used, the frequency of homopolymer repeats, or other distribution characteristics. For example, if in an example binary encoding scheme A is used to represent 0 and T is used to represent 1, then the middle region 206 can only include As and Ts. This limited set of nucleotides is a known characteristic of the polynucleotide strand 202. As a different example, a rolling code may be used to encode 0 and 1 in a way that prevents homopolymer repeats even when encoding a long string of 0s or 1s.

The raw data 212 is information coming from the sensor (s) 116 of the polynucleotide sequencer 102 prior to analysis by a base-calling algorithm. The type of raw data 212 will depend on the type of sensor(s) 116. For example, the nanopore sequencer MinION™ outputs binary files in the HDF5 format which includes "squiggle plots" of fluctuating electrical signals. Sequencing-by-synthesis platforms such as Illumina® sequencers generate a series of images, one for each round of polynucleotide extension, as the raw data. Other types of sensor(s) 116 used in polynucleotide sequencers 102 of different designs will generate different types of raw data 212 as understood by one of ordinary skill in the art.

The raw data 212 is then processed by a base-calling algorithm to assign base calls to portions of the raw data 212. The same raw data 212 can generate very different sequences depending on the base-calling algorithm used. Thus, the ultimate output from the polynucleotide sequencer 102 depends not just on hardware such as the sensor(s) 116 or software such as a base-calling algorithm 122, 124 but on the combination of both working together. As is evident from FIG. 1, the raw data 212 is generated at the polynucleotide sequencer 102 but may be passed to a base calling algorithm for analysis at a different component of the polynucleotide sequencing system 100 such as the local computing device(s) 104 or the remote computing device(s) 110.

In this example process 200, the raw data 212 may be provided to the default base-calling algorithm 122, the custom base-calling algorithm 124, or any number of alternative base-calling algorithms represented here as the Nth custom base-calling algorithm 214. The default base-calling algorithm 122 and the custom base-calling algorithm 124 may be the same as those introduced in FIG. 1. Differences among the base-calling algorithms include the factors considered or weights applied to probabilities of different base calls for particular nucleotides. The differences may also include how the base-calling algorithms are trained, how the base-calling algorithms calibrate or develop a baseline, how the base-calling algorithms assign a probability to a particular base call, and the like. The source of the difference between the custom base-calling algorithm 124 and the default base-calling algorithm 122 can be knowledge of the structure or content of the polynucleotide strand 202. The default base-calling algorithm 122 may be designed for sequencing of natural polynucleotides without any prior knowledge of the polynucleotide that will be sequenced. In contrast, the custom base-calling algorithm 124 is specific to the polynucleotide strand 202 because the design of the custom base-calling algorithm 124 incorporates and is based on knowledge about the polynucleotide strand 202 that is to be sequenced.

"Polynucleotide sequence data" is the electronic data generated by a polynucleotide sequencer system 100 that represents the nucleotides in the polynucleotide strand 202 as interpreted by the polynucleotide sequencer system 100. The default base-calling algorithm 122 generates polynucleotide sequence data 216 from the raw data 212. This polynucleotide sequence data 216 is not the same as the actual sequence of the polynucleotide strand 202. There are errors in this polynucleotide sequence data 216. In this example, the polynucleotide sequence data 218 generated by the custom base-calling algorithm 124 accurately identifies the nucleotides in the polynucleotide strand 202. There can be multiple ways to customize a base-calling algorithm based on information about the polynucleotide strand 202. The Nth custom base-calling algorithm 214 represents a different customization than the custom base-calling algorithm 124. In this example, the polynucleotide sequence data 220 generated by the Nth custom base-calling algorithm 214 includes inaccurate base calls. The differences between different customized base-calling algorithms 124, 214 may include things such as consideration of strand layout format 204 or not, consideration of nucleotide distribution or not, as well as modifying different portions of the default base-calling algorithm 122 such as modifying calibration versus modifying probabilities assigned to path weights through a model. For example, if the known characteristic is absence of homopolymers, the default base-calling algorithm may interpret a signal so that a homopolymer is called, but the custom base-calling algorithm may interpret the same signal so that homopolymers are not called.

Figure 3:
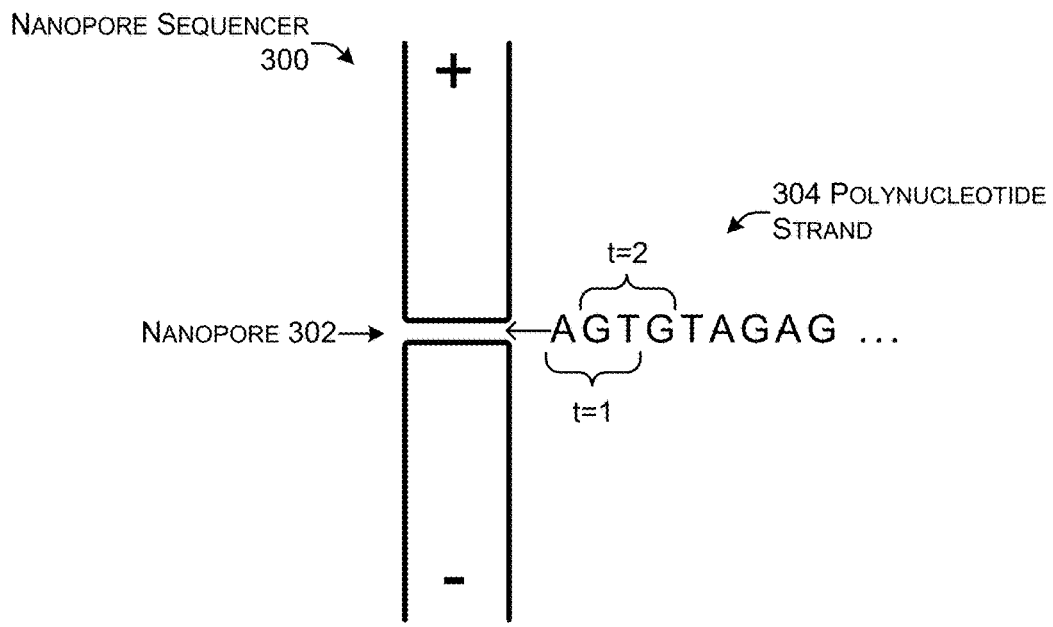
FIG. 3 shows modification of base-calling possibilities applied to nanopore sequencing.
Figure 3:
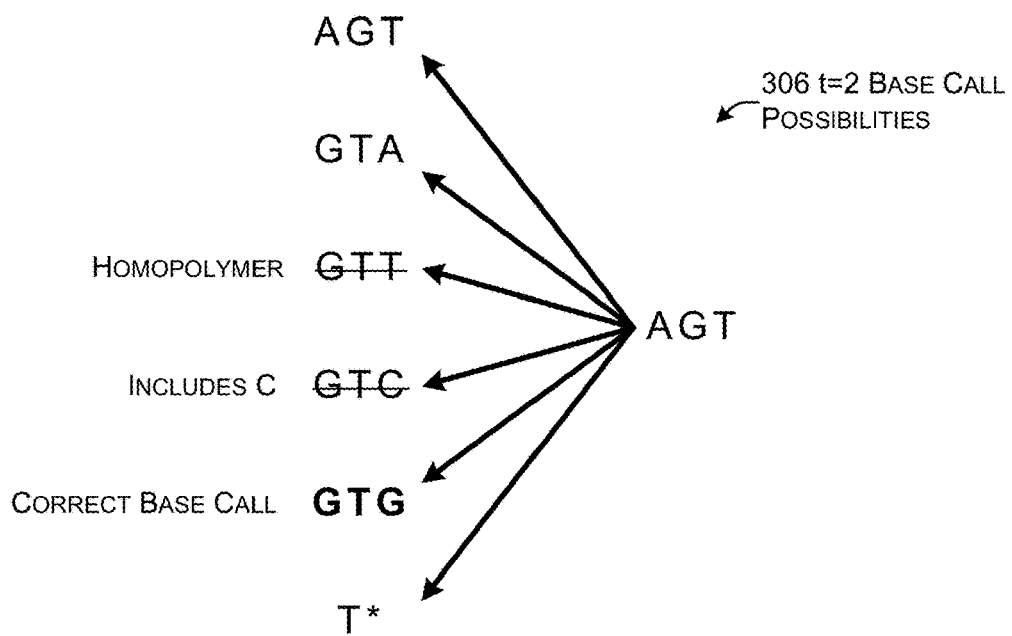

FIG. 3 shows modified analysis of base calls generated by a nanopore sequencer 300. A nanopore 302 is a small hole, of the order of 1 nanometer in diameter. Immersion of a nanopore 302 in a conducting fluid and application of a potential across it results in a slight electrical current due to conduction of ions through the nanopore 302. The amount of current which flows is sensitive to the size of the nanopore 302. As the polynucleotide strand 304 passes through the nanopore 302 it partially blocks the flow of electric current through the nanopore 302. The flow of current is sampled over time which is the observable output, the raw data, of the system. The central idea is that the single-stranded polynucleotide product present in the nanopore 302 affects the current in a way that is strong enough to enable decoding the electric signal data into a base sequence.

For nanopore sequencing, first, the polynucleotide strand 304 is sheared into fragments of 8-20 Kbp and adapters are ligated to either end of the fragments. The resulting fragments pass through a protein embedded in a membrane via a nanometer-sized channel (biological nanopore). A single strand of the polynucleotide strand 304 passes through the nanopore 302; the optional use of a hairpin adapter at one end of the fragment allows the two complementary strands of polynucleotide strand 304 to serially pass through the nanopore 302, allowing two measurements of the fragment creating a "2d read." The first strand going through the nanopore 302 can be called the template, and the second, complementary strand can be called the complement.

The process of base calling nanopore systems, takes as input a list of electrical current measurements, and produces as output a list of bases most likely to have generated those currents. In this example, the first three bases read from the polynucleotide strand 304 at time=1 are AGT. The next three bases in the polynucleotide strand 304 at time=2 are GTG. The base call possibilities 306 that may have generated the electrical signal at time=2 are AGT, GTA, GTT, GTC, GTG, and T*. The base-calling algorithm identifies the most probable combination of bases. If, for example, it is known that the polynucleotide strand 304 does not include homopolymer repeats and that knowledge is used to modify the base-calling algorithm, then the option GTT can be excluded because it is known to be incorrect. As a further example, if the polynucleotide strand 304 is synthesized without C, then the option GTC can be excluded because that base call would be incorrect. Thus, by excluding known incorrect possibilities, the base-calling algorithm as modified is more likely to identify the correct base call. As applied to a base-calling algorithm, the HMM process which may be used for base calling in a nanopore sequencer finds a path of maximal likelihood through a probability model. Excluding possibilities from the range of paths through the model makes the HMM more accurate and thus the path identified is more likely to be correct resulting in correct base calls.

Figure 4:
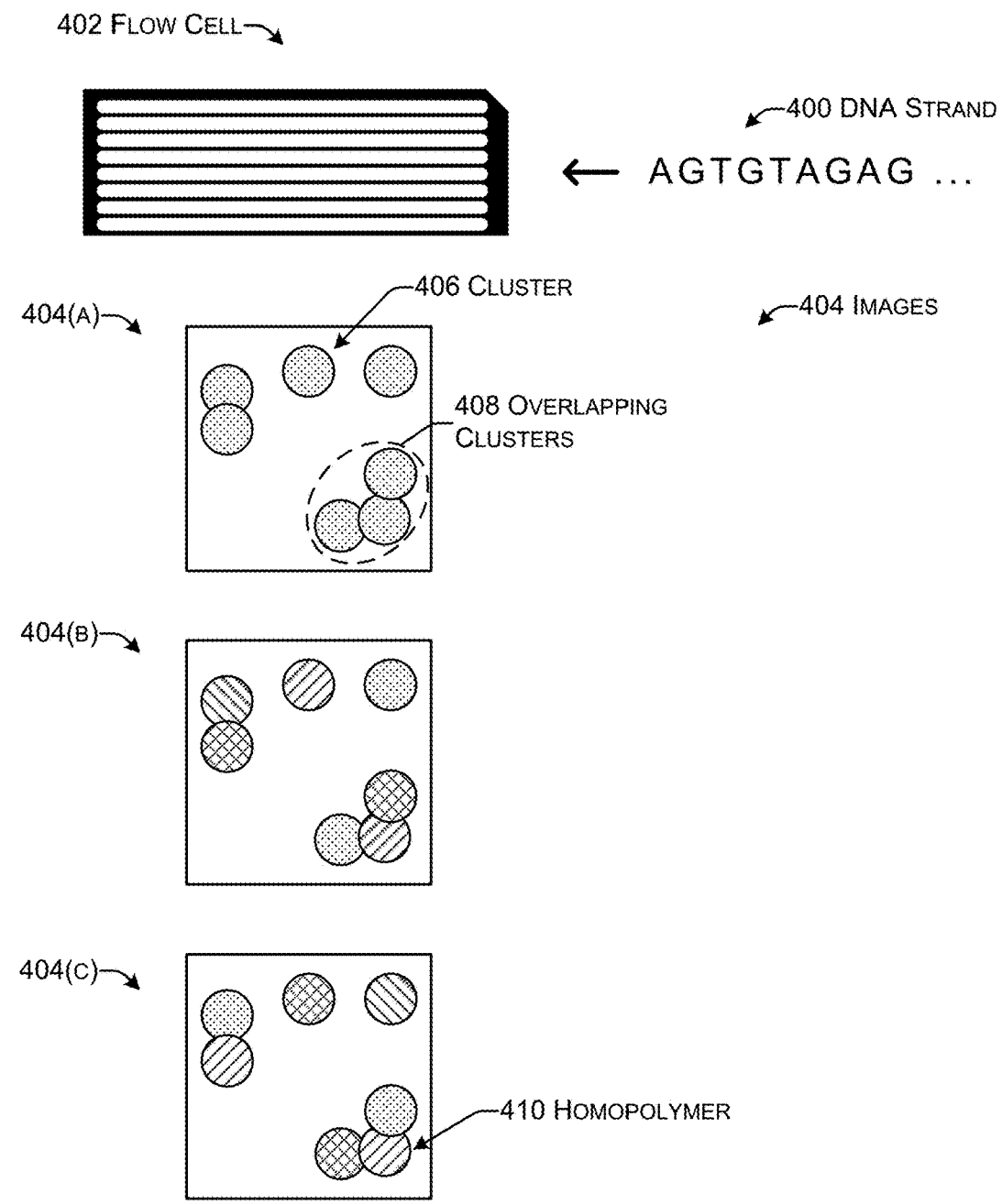
FIG. 4 shows modification of base-calling possibilities applied to sequencing-by-synthesis.

FIG. 4 shows modified analysis of base calls generated by a polynucleotide sequencer that uses sequencing-by-synthesis. Sequencing-by-synthesis is based on the amplification of DNA on a solid surface using fold-back PCR and anchored primers. A DNA strand 400 is fragmented, and adapters are added to the 5'- and 3'-ends of the fragments. For genomic DNA, each of the fragments is expected to have little or no similarity to other fragments. However, for a population of artificial DNA, every fragment in the population may be partially identical if, for example, all the artificial DNA strands are synthesized to have the same primer binding site. An adapter can include a sequence of nucleotides that can bind to complementary sequences on the surface of the flow cell 402 that is used in the sequencing process. The adapters are added to polynucleotides such that each polynucleotide binds to a different location on the surface of the flow cell 402. DNA fragments that are attached to the surface of a flow cell 402 are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell. Primers, DNA polymerase, and four fluorophore-labeled, reversibly terminating nucleotides are used to perform sequential sequencing. After nucleotide incorporation, one or more lasers are used to excite the fluorophores, and an image is captured by a camera which may be the sensor(s) 116 introduced in FIG. 1. The 3' terminators and fluorophores from each incorporated base are removed and the incorporation, detection, and identification steps are repeated. This creates a time series of images 404 in which the order of the images 404, the colors detected on the images 404, and location of color clusters on the images 404 provide the basis for identifying the polynucleotide sequence.

As described above, sequencing-by-synthesis adds fluorescently labeled nucleotides to the polynucleotides in the clusters of the flow cell 402. The fluorescently labeled nucleotides can be added using a sequencing primer that has been added to a complementary region of each polynucleotide to be sequenced. Each type of nucleotide found in DNA, or RNA in some situations, can be coupled to a different fluorophore using a cleavable bond. For example, each type of nucleotide, G, C, A, T, or U in the case of RNA, can be associated with a respective fluorophore. The different fluorophores coupled to the nucleotides can emit electromagnetic radiation at different wavelength distributions. The different wavelength distributions of the fluorophores can be associated with different colors. For example, a first fluorophore can emit electromagnetic radiation at a first set of wavelengths and a second fluorophore can emit electromagnetic radiation at a second set of wavelengths. The first set of wavelengths can be different from the second set of wavelengths, although, in some cases, the first set of wavelengths and the second set of wavelengths can have some overlap. In some situations, one type of nucleotide may not be bound to a respective fluorophore and this type of nucleotide can be detected based on the absence of radiation emission.

Sequencing-by-synthesis can take place over a number of rounds with each round determining the nucleotides located at a particular position of the sequences of the polynucleotides being sequenced. During each round of sequencing, a single fluorophore-bound nucleotide is added to a complementary nucleotide of each polynucleotide. The polynucleotides are then exposed to electromagnetic radiation, such as via a laser. Upon excitation by the electromagnetic radiation, the fluorophores attached to the nucleotides that have been added emit electromagnetic radiation having certain wavelengths. A camera can capture images of the flow cell during the application of electromagnetic radiation and the images can include regions of illumination for each polynucleotide. The regions of illumination can be associated with different colors based on the nucleotide at a respective position of the polynucleotides. Thus, the images can be analyzed using machine-vision techniques to determine which portions of the captured images correspond to clusters of polynucleotides based on the location of illumination and the wavelengths emitted by the various fluorophores. For example, clusters emitting at a first distribution of wavelengths (e.g., wavelengths corresponding to a red color) can be associated with a first type of nucleotide (e.g., thymine) and clusters emitting at a second distribution of wavelengths (e.g., wavelengths corresponding to a green color) can be associated with a second type of nucleotide (e.g., guanine). Sequence diversity between the various clusters bound to the flow cell results in a diversity of colors emitted by the fluorophores and detected by the camera. By continuing to add complementary fluorophore-bound nucleotides to the polynucleotides being sequenced, applying electromagnetic radiation, and analyzing images of the flow cell 402, the arrangement of nucleotides for each polynucleotide can be determined.

Part of making base calls from the data generated by sequencing-by-synthesis is analyzing the images 404 captured by the camera to identify the locations of each individual cluster 406 on the flow cell 402. When two adjacent clusters 406 are different colors it is easier to distinguish the separate cluster boundaries than when the adjacent clusters 406 are the same color. The calibration process can include analyzing a certain number of images 404 at the beginning of each polynucleotide being sequenced in order to locate the clusters 406 on the flow cell 402. The region of the polynucleotides used during the calibration process can be referred to herein as a "calibration region." Typical base-calling algorithms are designed to expect about an equal distribution for each type of nucleotide for a given round of sequencing because this ratio of nucleotides is common in naturally occurring DNA. Equal distribution of nucleotides at a given position among all the DNA molecules bound to a flow cell 402 increases the probability that adjacent clusters 406 will have different colors and be distinguishable from one another. To illustrate, for DNA, the polynucleotide sequencer can expect to determine that, for each sequencing round, about 25% of clusters will be associated with A, about 25% of clusters will be associated with T, about 25% of clusters will be associated with G, and about 25% of clusters will be associated with C on each image 404.

Cluster 406 positions are fixed based on where the DNA strands 400 bind on the flow cell 402. Identification of clusters 406 is challenging due to interpretation of the images 404. If all the DNA strands 400 placed on the flow cell 402 have the same sequence at the beginning, such as a common primer binding site, then nearly every cluster 406 will have the same color in the image 404(a) making identification of clusters difficult if there is a group of overlapping clusters 408. Although cluster formation is sometimes identified as a step separate from base calling, in this disclosure cluster formation is considered part of base calling because it occurs after capture of the raw data and before generating polynucleotide sequence data. Knowledge of characteristics of the DNA strand 400, such as a strand layout format that identifies regions having higher nucleotide diversity (i.e., inter-nucleotide diversity at a same position in multiple polynucleotide strands), may be used by the base-calling algorithm to select a different set of images 404 from an area of higher nucleotide diversity as the basis for identifying clusters. For example, in an image 404(b) captured from a portion of the DNA strand 400 where there is greater nucleotide diversity, adjacent and even overlapping clusters 408 can be more readily distinguished. Once the cluster boundaries are established, the image 404(a) of a low diversity region such as a primer binding site can then be analyzed using established cluster boundaries. This type of modification of the base-calling algorithm takes advantage of knowledge about how nucleotide diversity varies across different regions of a polynucleotide strand according to a known strand layout format.

FIG. 4 shows black-and-white patterns representing the different colors, including absence of color, that are emitted by the excited fluorophores. However, distinguishing the wavelength of color in an actual image 404 may be ambiguous. If known rules about the allowable sequence of the DNA strand 400 can guide the base-calling algorithm, ambiguous clusters 406 may be properly identified by elimination of options that are not allowed given knowledge about the structure of an artificial polynucleotide. For example, if image 404(c) comes subsequent in time to image 404(b) then the same color detected in the same cluster 406 represents a homopolymer 410. Assuming that the DNA strand 404 was synthesized without homopolymer repeats, it is known that this homopolymer 410 is an incorrect base call. Therefore the base-calling algorithm can be modified to make a different base call, such as picking the second most probable base when the most probable would result in a homopolymer repeat.

Illustrative Processes

For ease of understanding, the processes discussed in this disclosure are delineated as separate operations represented as independent blocks. However, these separately delineated operations should not be construed as necessarily order dependent in their performance. The order in which the process is described is not intended to be construed as a limitation, and any number of the described process blocks may be combined in any order to implement the process, or an alternate process. Moreover, it is also possible that one or more of the provided operations may be modified or omitted.

Figure 5:
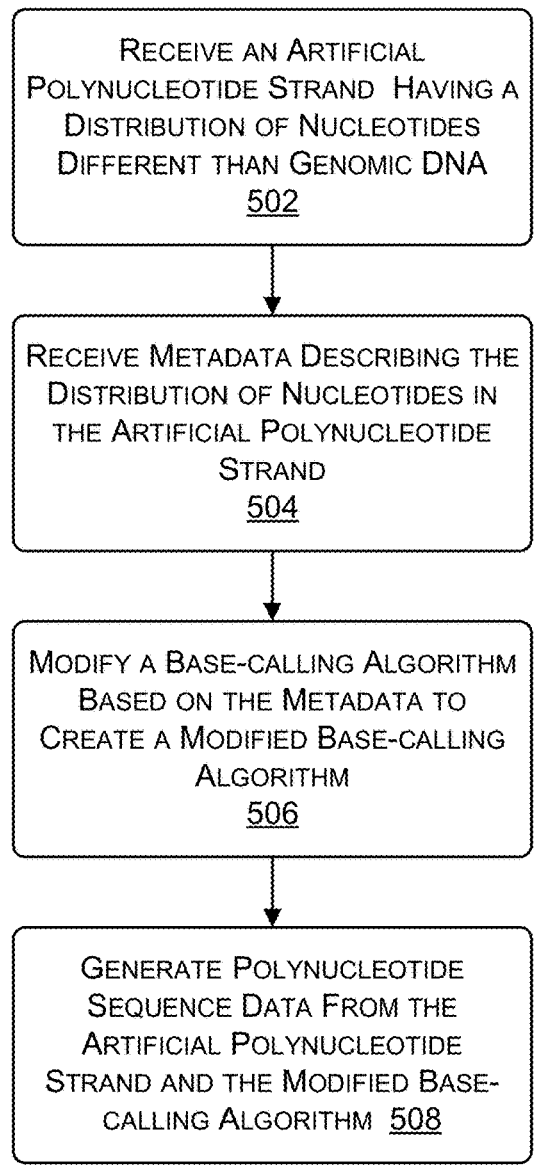
FIG. 5 shows an illustrative process for generating polynucleotide sequence data with a modified base-calling algorithm.

FIG. 5 shows an illustrative process 500 for generating sequence data from an artificial polynucleotide strand using a modified base-calling algorithm. The artificial polynucleotide strand may be the polynucleotide strand 114 from FIG. 1, the polynucleotide strand 202 from FIG. 2, the polynucleotide strand 304 FIG. 3, or the DNA strand 400 from FIG. 4.

At 502, the artificial polynucleotide strand is received. The artificial polynucleotide strand may be received by a user placing the artificial polynucleotide strand within a polynucleotide sequencer. The artificial polynucleotide strand may have a distribution of nucleotides different than a natural polynucleotide. For example, the artificial polynucleotide strand may have a distribution of nucleotides different than genomic DNA. The artificial polynucleotide strand may have a distribution of nucleotides in which the frequency of occurrence of one or more of the natural nucleotide bases is less than 20%, less than 15%, or less than 10%. Additionally or alternatively the artificial polynucleotide strand may have a distribution nucleotides in which the frequency of occurrence of one or more of the natural nucleotide bases is more than 30%, more than 35%, or more than 40%. The artificial polynucleotide strand may also have a distribution of nucleotide bases that varies throughout different portions of the artificial polynucleotide strand by more than a threshold amount. For example, the frequency of nucleotide A in a first portion of the artificial polynucleotide strand may be more than 10%, more than 20%, or more than 30% higher than the frequency of A in a second portion of the artificial polynucleotide strand.

In an implementation, the artificial polynucleotide strand can be a synthetic polynucleotide strand beginning and ending with primer binding regions including a payload region in the middle that encodes binary data. A synthetic polynucleotide may be created by chemical or enzymatic synthesis. In one implementation, a synthetic polynucleotide can be created by an oligonucleotide synthesizer such as Dr. Oligo™ available from Biolytic® Lab Performance, Inc. Thus, the artificial polynucleotide strand may be designed expressly for storage of binary data, and thus, due to this intentional design it has an arrangement and distribution of nucleotides that differs from a natural polynucleotide. However, because the artificial polynucleotide strand was intentionally designed according to a schema, certain characteristics of that artificial polynucleotide strand are known. In one implementation, the payload region may encode binary data through use of a rolling code that prevents homopolymer repeats.

At 504, metadata describing the distribution of nucleotides in the artificial polynucleotide strand is received. This metadata may be received as an electronic file provided to a polynucleotide sequencer or associated computing device such as the local computing device(s) 104 and/or the remote computing device(s) 110 shown in FIG. 1. The metadata may be provided at the same or substantially the same time that the artificial polynucleotide strand itself is provided to the polynucleotide sequencer. Alternatively, the metadata may be provided before or after the artificial polynucleotide strand is provided. For example, artificial polynucleotides may encode digital data according to multiple different encoding schemes. The effect that each of these encoding schemes has on the distribution of nucleotides in an artificial polynucleotide is stored as metadata. Thus, when a particular artificial polynucleotide is retrieved for the purpose of sequencing to decode the binary information, the relevant metadata may be accessed based on the encoding scheme used for encoding the binary information. In one example implementation, many different types of metadata may be stored in the remote computing device(s) 110. The metadata may also be provided after analysis of the polynucleotide by the polynucleotide sequencer such as through electronic files, removable media, etc. Thus, there may be a temporal gap between the polynucleotide sequencer obtaining raw data from reading the artificial polynucleotides strand, such as the raw data 212 described in FIG. 2, and subsequent base calling.

The metadata may indicate a high-diversity region of the artificial polynucleotide strand. For example, the metadata can indicate that a middle region 206 of a strand layout format 204 of the artificial polynucleotide has high diversity meaning that throughout a population of artificial polynucleotides, there is a roughly equal distribution of A, G, C, and T. The metadata may also include an indication of a known partial sequence that is shared by all of the artificial polynucleotide strands. For example, the known partial sequence may be a primer binding region that is known to be included at the same position in all polynucleotide strands within a sample. Complete identity at a particular location along the polynucleotide strand amongst all polynucleotide strands in a population is low diversity to the point of being no diversity whatsoever. In an implementation, the metadata may include a list of nucleotide bases present in artificial polynucleotide strand. Presence in a list does not imply an ordered list or any particular data structure. The list may identify all four of the natural nucleotide bases for DNA or as the case may be RNA. If less than all the natural nucleotide bases are present, the list may identify only two or three nucleotide bases present in the artificial polynucleotide strand. Alternatively, if unnatural nucleotide bases are included, then the identity of which unnatural nucleotide bases are present can be included in the list. This list provides the "alphabet" from which the artificial polynucleotides strand is built. The list may apply to only a portion of an artificial polynucleotide strand (e.g., payload region does not include T), an entire artificial polynucleotide strand, or a population of multiple artificial polynucleotide strands. Alphabets that use less than all of the natural polynucleotide bases and one or more unnatural polynucleotide bases are also possible.

The metadata can include an error profile associated with a polynucleotide sequencer that will be used to generate the polynucleotide sequence data. The error profile can be obtained from prior calibration tests of the polynucleotide sequencer. The error profile may be device specific, that is, the error profile may be unique to an individual polynucleotide sequencer and different from other polynucleotide sequencers even of an identical model. Additionally, the error profile can be associated with a method was used to synthesize the artificial polynucleotide strand. Oligonucleotide synthesis methods are associated with synthesis errors (e.g., deletions, insertions, and substitutions) that vary with the particular synthesis method. The effort profiles from synthesis may also be used to change the base-calling algorithm due to known/expected errors in the sequence itself. The error profile is not necessarily based on a characteristic of the artificial polynucleotide strand. However, the error profile can be based on differences between polynucleotide sequence data generated from sequencing a region of the artificial polynucleotide strand having a known sequence to that actual known sequence itself. This metadata may be generated mid-run after sequencing the region with the known sequence and used to modify the base-calling algorithm for analysis of other regions of the artificial polynucleotide strand.

The metadata can include an analysis direction of the artificial polynucleotide strand. The metadata can also include information density of the artificial polynucleotide strand, a precision standard for the artificial polynucleotide strand or a length of the artificial polynucleotide strand. Metadata containing a precision standard together with data on composition can be used to change the base-calling algorithm by accounting for expected errors. For example, if the metadata describes percentages of the respective bases, A, G, C, and T, then the base-calling algorithm will be changed to call bases for the polynucleotide strand so that the sequence data includes the same base percentages as described in the metadata. Metadata can also serve as a baseline for errors identifying due to sequencing rather than due to synthesis of the polynucleotide and help correct the errors by modifying base-calling.

At 506, a base-calling algorithm is modified based on the metadata received at 504 to create a modified base-calling algorithm. The base-calling algorithm, prior to modification, may be the default base-calling algorithm 122 introduced in FIG. 1. The modified base-calling algorithm may be the same as the custom base-calling algorithm 124 introduced in FIG. 1. In an implementation, the base-calling algorithm can call individual bases using a model in which each individual base has an equal probability of being one of adenine (A), guanine (G), cytosine (C), or thymine (T). The equal probability may be represented by each of four bases having a 25% probability of being present at a given position or by each of the four bases having the same range of probabilities such as between about 20 to 30%, about 22 to 28%, about 24 to 26%, or about 24.5 to 25.5%. In an implementation, the modified base-calling algorithm can call individual bases using a model in which each individual base has an unequal probability of being one of adenine (A), guanine (G), cytosine (C), or thymine (T). The unequal probability can be represented by one of the bases A, G, C, or T having a different probability of being present at a given position than another one of the bases. The difference in probability could be greater than 5, 10, 15, 20, or 25%. For example, a 50% probability of an A being present and a 30% probability of a G being present is a 20% difference representing an unequal probability. There is an unequal probability between A and G being present in this example even if there is an equal probability of T and C both being present at 10%. Thus, there does not need to be unequal probabilities between all the bases for there to be an unequal probability of being one of A, G, C, or T.

The modifications to the base-calling algorithm may include, but are not limited to, modifying a probability of calling a particular base, modifying a probability of a transition through a graph (e.g. HMM) used to correlate a signal with a base call, modifying a bias for choosing between two, or more, possible base calls, etc. In an implementation, the modifications may include using a specified region of the artificial polynucleotide strand for calibration of the base calling algorithm. The specified region may be a high-diversity region of the artificial polynucleotide. If a partial sequence of the artificial polynucleotide strand is known, the modifications may limit base calls over a region of the artificial polynucleotide strand so that the base calls match the known partial sequence. The region is the portion of the artificial polynucleotide strand that contains the known sequence. The modifications can include changing the base-calling algorithm to select base calls from a list of bases present in the artificial polynucleotide strand. That list can include fewer than all of the natural bases or can include unnatural bases in addition to the natural bases.

At 508, polynucleotide sequence data is generated from the artificial polynucleotide strand and the modified base-calling algorithm resulting from the modifications at 506. One example of polynucleotide sequence data is the polynucleotide sequence data 218 introduced in FIG. 2. The polynucleotide sequence data is a digital representation of the nucleotide base sequence of the polynucleotide strand received at 502. Although the "data" is an electronic representation often presented using a string of alphabetic characters (i.e., A, G, C, and T or U) the polynucleotide sequence data is derived from measured physical characteristics of a polymeric molecule. Specifically, the polynucleotide sequence data is generated from the combination of signals received from a sensor, such as the sensor(s) 116 included in the polynucleotide sequencer 102, and analysis of the signals which is performed in part by a base-calling algorithm such as the custom base-calling algorithm 124.

Figure 6:
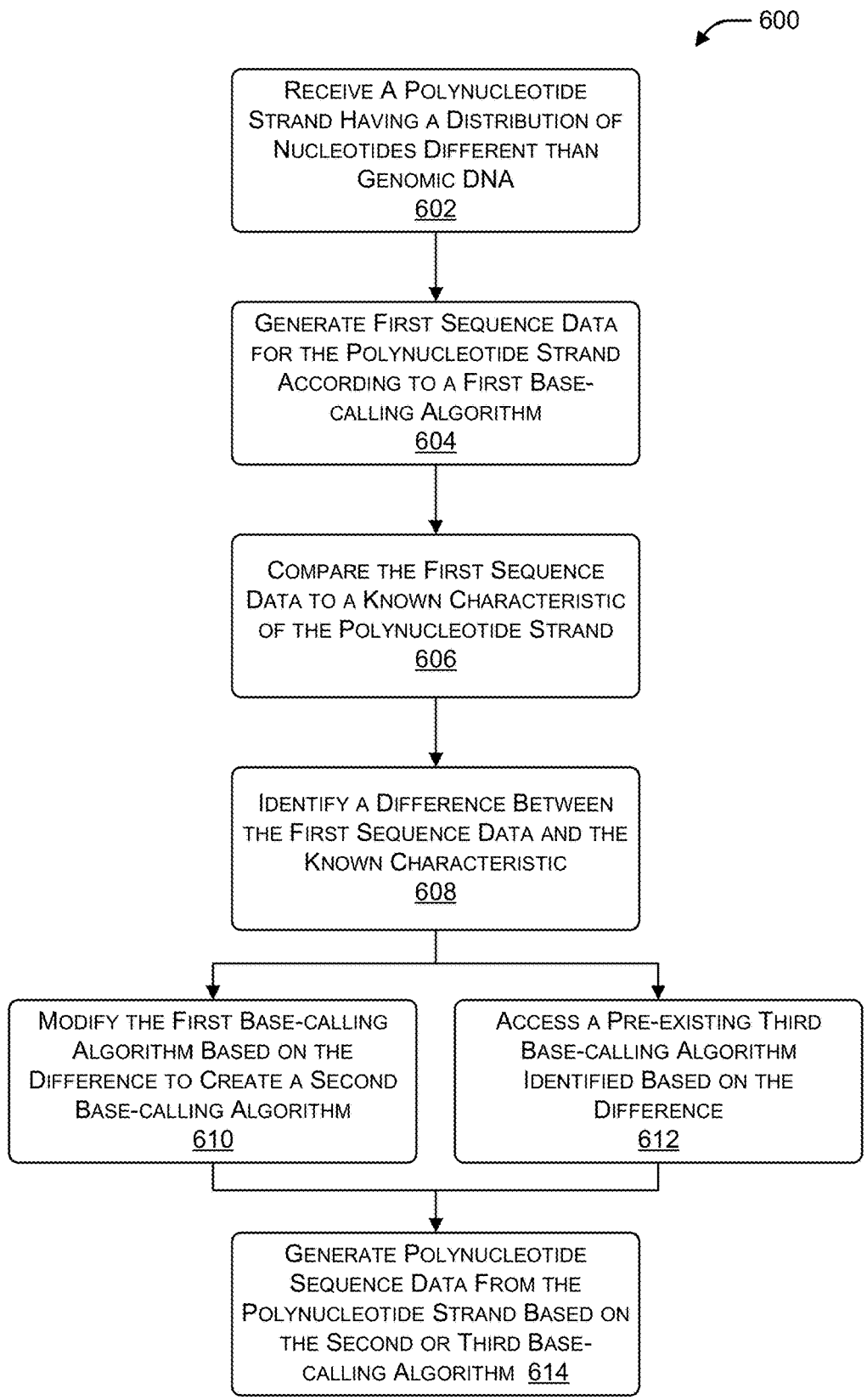
FIG. 6 shows an illustrative process for generating polynucleotide sequence data using a known characteristic of a polynucleotide strand.

FIG. 6 shows an illustrative process 600 for generating sequence data using a known characteristic of a polynucleotide strand. The polynucleotide strand may be an artificial polynucleotide strand, such as the polynucleotide strand 114 from FIG. 1, the polynucleotide strand 202 from FIG. 2, the polynucleotide strand 304 from FIG. 3, or the DNA strand 400 from FIG. 4. The polynucleotide strand can be a natural polynucleotide strand having a known characteristic.

At 602, the polynucleotide strand is received. The polynucleotide strand can have a distribution of nucleotides different than a natural polynucleotide. For example, the polynucleotide strand may have a distribution of nucleotides in which the frequency of occurrence of one or more of the natural nucleotide bases is less than 20%, less than 15%, or less than 10%. Additionally or alternatively, the artificial polynucleotide strand may have a distribution of nucleotides in which the frequency of occurrence of one or more of the natural nucleotide bases is more than 30%, more than 35%, or more than 40%. The polynucleotide strand may also have a distribution of nucleotide bases that varies throughout different portions of the polynucleotide strand by more than a threshold amount. For example, the frequency of nucleotide A in a first portion of the polynucleotide strand may be more than 10%, more than 20%, or more than 30% higher than the frequency of A and a second portion of the polynucleotide strand. The polynucleotide strand can be included in a population of polynucleotide strands, the population of polynucleotide strands as a whole having an intra-strand distribution of nucleotides different than a population of nucleotide strands obtained from genomic DNA or mRNA. For example, all polynucleotide strands in the population may have the same nucleotides at the first n bases.

In an implementation, the polynucleotide strand can be an artificial polynucleotide strand beginning and ending with primer binding regions including a payload region in the middle that encodes binary data. Thus, the polynucleotide strand may be designed expressly for storage of binary data, and thus, due to this intentional design it has an arrangement and distribution of nucleotides both intra-nucleotide and inter-nucleotide that differs from natural polynucleotides. However, because the polynucleotide strand was intentionally designed according to a schema, certain characteristics of that artificial polynucleotide strand are known. In one implementation, the payload region may encode binary data through use of a rolling code that prevents homopolymer repeats.

At 604, first sequence data for the polynucleotide strand is generated according to a first base-calling algorithm. The first base-calling algorithm may be the default base-calling algorithm 122 introduced in FIG. 2. The first base-calling algorithm may generate sequence data that includes inaccuracies because the first base-calling algorithm is designed for sequencing polynucleotides with different characteristics than the polynucleotide strand, specifically designed for sequencing natural polynucleotides.

At 606, the first sequence data is compared to the known characteristic of the polynucleotide strand. The known characteristic may be a length of the polynucleotide strand, a list of nucleotide bases present in the polynucleotide strand, frequencies of the nucleotide bases included in the polynucleotide strand, variations in nucleotide diversity across regions of the polynucleotide strand, or any other characteristic discussed in this disclosure. The comparison may include sequence alignment or partial sequence alignments.

At 608, a difference is identified between the first sequence data and the known characteristic. The difference can be a base call in the first sequence data that differs from the known characteristic of the polynucleotide strand. The difference can be a frequency of a nucleotide base in the sequence data (e.g., 20% G vs. 25% G), a difference in region-specific nucleotide diversity, a difference in strand length, or any other difference. For example, if the known characteristic is a list of bases used in the polynucleotide strand, the difference could be presence of a nucleotide base in the first sequence data that, based on the known characteristic, is not present in the polynucleotide strand or absence of a synthetic nucleotide base in the first sequence data that, based on the known characteristic, is present in the polynucleotide strand. Any identified difference can suggest that the first base-calling algorithm is not producing accurate results because a known characteristic of the polynucleotide strand is absent in the sequence data. Multiple differences can be identified. For example, presence of homopolymers repeats (when a known characteristic is absence of homopolymer repeats) and uniform GC % (when a known characteristic is variation of GC % between a first region and a second region) can both be identified as differences.

At 610, the first base-calling algorithm is modified based on the difference to create a second base-calling algorithm. The modifications can take account of all differences identified at 608. The modifications to the base-calling algorithm may include, but are not limited to, modifying a probability of calling a particular base, modifying a probability of a transition through a graph (e.g. HMM) used to correlate a signal with a base call, modifying a bias for choosing between two, or more, possible base calls, etc.

Alternatively at 612, a third base-calling algorithm that is pre-existing and does not need to be crated can be identified. There may be multiple pre-existing base-calling algorithms that can be accessed and each of the pre-existing base-calling algorithms may differ from a standard base-calling algorithm in at least one way to account for a particular difference (e.g., a base-calling algorithm for the absence of homopolymers, a different base-calling algorithm for a GC % greater than 75%, etc.), The pre-existing base calling algorithm may be identified based on the difference between the first sequence data and the known characteristic.

If the difference is frequency of a nucleotide base, the first base-calling algorithm can be modified by changing a probability associated with the nucleotide base being included in the polynucleotide strand. If the difference is strand length, the modification may alter how phasing is handled by the first-base calling algorithm. If the difference is region-specific nucleotide diversity, then the modification may assign a correspondence between at least two regions of the polynucleotide sequence and at least two corresponding target nucleotide diversities. For example, if a first region of a population of polynucleotide strands is not diverse (e.g., corresponds to a primer binding site), then the modifications may cause the second base-calling algorithm to call the bases for all of the polynucleotide strands the same in the first region while in a second highly diverse region (e.g., a payload region), the second base-calling algorithm may use base calling appropriate for genomic DNA. The first region as a not diverse region can be assigned a diversity indicating that at least a threshold percent of all polynucleotide strands in a set of polynucleotide strands include a same nucleotide base at the same position. The threshold percent can be 100% indicating that every polynucleotide strand in the set has the same sequence or a lower percentage such as 99, 98, 97, 96, 95, or 90% recognizing biological variability, contamination, or lack of fidelity in oligonucleotide synthesis. The second highly diverse region may be assigned a diversity indicating that all polynucleotide strands in the set of polynucleotide strands have an about equal distribution (e.g., about 25%, about 22 to 28%, etc.) at any given position in the second region.

At 614, polynucleotide sequence data is generated from the polynucleotide strand based on the second base-calling algorithm or the third base-calling algorithm. One example of polynucleotide sequence data is the polynucleotide sequence data 218 introduced in FIG. 2. The polynucleotide sequence data is a digital representation of the nucleotide base sequence of the polynucleotide strand received at 602. Although the "data" is an electronic representation often presented using a string of alphabetic characters (i.e., A, G, C, and T or U) the polynucleotide sequence data is derived from measured physical characteristics of a polymeric molecule. Specifically, the polynucleotide sequence data is generated from the combination of signals received from a sensor, such as the sensor(s) 116 included in the polynucleotide sequencer 102, and analysis of the signals which is performed in part by a base-calling algorithm, such as the custom base-calling algorithm 124.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document, "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A method for sequencing an artificial polymer comprising: receiving the artificial polymer having a distribution of nucleotides different than a natural polynucleotide; receiving metadata describing the distribution of nucleotides in the artificial polymer; modifying a base-calling algorithm based on the metadata to create a modified base-calling algorithm; and generating polynucleotide sequence data from the artificial polymer based on the modified base-calling algorithm.

Clause 2. The method of clause 1, wherein the artificial polymer is an artificial polymer beginning and ending with primer binding regions and including a payload region in the middle that encodes binary data.

Clause 3. The method of clause 1 or 2, wherein the metadata comprises an indication of a high-diversity region of the artificial polymer and the modified base-calling algorithm uses reads from the high-diversity region for calibration of base calling.

Clause 4. The method of any of clauses 1-3, wherein the metadata comprises an indication of a known partial sequence of the artificial polymer, and the modified base-calling algorithm is limited to making base calls over a region of the artificial polymer that match the known partial sequence.

Clause 5. The method of any of clauses 1-4, wherein the metadata comprises a list of nucleotide bases present in the artificial polymer and the modified base-calling algorithm makes base calls from the list.

Clause 6. The method of any of clauses 1-5, wherein the metadata comprises at least one of analysis direction of the artificial polymer, information density of the artificial polymer, a precision standard for the artificial polymer, or a length of the artificial polymer.

Clause 7. The method of any of clauses 1-6, wherein the base-calling algorithm calls individual bases using a model in which each individual base has a probability between about 22 to 28% of being adenine (A), between about 22 to 28% of being guanine (G), between about 22 to 28% of being cytosine (C), and between about 22 to 28% of being thymine (T) and the modified base-calling algorithm calls individual bases using a model in which each individual base has a greater than 15% difference in probability of being one of A, G, C, or T.

Clause 8. The method of any of clauses 1-7, wherein the artificial polymer comprises an artificial polynucleotide strand.

Clause 9. The method of clause 8, wherein the polynucleotide strand comprised DNA.

Clause 10. The method of any of clauses 1-7, wherein the artificial polymer comprises an artificial amino acid strand or an artificial carbohydrate polymer.

Clause 11. The method of any of clauses 1-7 wherein the artificial polymer comprises a nonnatural sequence-controlled polymer.

Clause 12. A polynucleotide sequencer system comprising: a sensor configured to generate a signal indicative of a nucleotide base associated with a sensed polynucleotide; computer-readable media comprising instructions that when executed by a processor cause the processor to: generate a custom base-calling algorithm based on a default base-calling algorithm and a known characteristic of the sensed polynucleotide provided to the polynucleotide sequencer system; and create sequence data based on the characteristics of the signal and the custom base-calling algorithm; and an output device configured to render the sequence data in a human-readable form.

Clause 13. The polynucleotide sequencer system of clause 12, wherein the sensor comprises a camera and the signal comprises a color detected by the camera.

Clause 14. The polynucleotide sequencer system of clause 12 or 13, wherein the sensor comprises an electrically resistant membrane having a nanopore and the signal comprises an electrical current.

Clause 15. The polynucleotide sequencer system of any of clauses 12-14, wherein the sensor comprises a complementary metal-oxide semiconductor (CMOS) and the signal comprises a change in pH.

Clause 16. The polynucleotide sequencer system of any of clauses 12-15, wherein the known characteristic is absence of homopolymers, the default base-calling algorithm interprets the signal so that a homopolymer is called, and the custom base-calling algorithm interprets the signal so that homopolymers are not called.

Clause 17. The polynucleotide sequencer system of any of clauses 12-16, wherein the signal as interpreted by the default base-calling algorithm is associated with a first set of probabilities corresponding to nucleotide bases of a natural polynucleotide and the custom base-calling algorithm uses a second set of probabilities that are based on the known characteristic of the sensed polynucleotide.

Clause 18. The polynucleotide sequencer system of any of clauses 12-17, wherein the known characteristic comprises at least one of a base order probability, a list of nucleotide bases present in the sensed polynucleotide, a length of the sensed polynucleotide, or a layout of the sensed polynucleotide.

Clause 19. The polynucleotide sequencer system of any of clauses 12-18, wherein the known characteristic comprises a list of nucleotide bases present in the sensed polynucleotide that include an unnatural base.

Clause 20. A method for correcting sequencing data based on a known characteristic of a polynucleotide strand, the method comprising: generating first sequence data for the polynucleotide strand according to a first base-calling algorithm; comparing the first sequence data to the known characteristic of the polynucleotide strand; identifying a difference between the first sequence data and the known characteristic; modifying the first base-calling algorithm based on the difference to create a second base-calling algorithm or accessing a pre-existing third base-calling algorithm identified based on the difference; and generating second sequence data for the polynucleotide strand according to the second base-calling algorithm or the third base-calling algorithm.

Clause 21. The method of clause 20, wherein the difference comprises a base call in the first sequence data differs from the known characteristic of the polynucleotide strand.

Clause 22. The method of clause 20 or 21, wherein the difference comprises a frequency of a nucleotide base and modifying the first base-calling algorithm comprises changing a probability associated with the nucleotide base being included in the polynucleotide strand.

Clause 23. The method of any of clauses 20-22, wherein the difference comprises region-specific nucleotide diversity and modifying the first base-calling algorithm comprises assigning a correspondence between at least two regions of the polynucleotide sequence and at least two corresponding target nucleotide diversities.

Clause 24. The method of any of clauses 20-23, wherein a first region of the at least two regions corresponds to a primer binding site and is assigned a diversity indicating that at least about 95% of all polynucleotide strands in a set of polynucleotide strands including the polynucleotide strand include a same nucleotide base at positions in the first region, and a second region of the at least two regions corresponds to a payload region and is assigned a diversity indicating that of all polynucleotide strands in the set of polynucleotide strands there is an about equal distribution of nucleotide bases at positions in the second region.

Clause 25. The method of any of clause 24, wherein the payload region stores digital data encoded in the order of polynucleotides of the payload region.

Clause 26. The method of any of clauses 20-25, wherein the difference comprises presence of a nucleotide base in the first sequence data that, based on the known characteristic, is not present in the polynucleotide strand or absence of a synthetic nucleotide base in the first sequence data that, based on the known characteristic, is present in the polynucleotide strand.

Clause 27. The method of any of clauses 20-26, wherein the known characteristic comprises strand length, the difference comprises a difference in strand length, and modifying the first-base calling algorithm comprises modifying a phasing of the first-base calling algorithm.

Clause 28. The method of any of clauses 20-27, further comprising receiving the polynucleotide strand, wherein the polynucleotide strand has a distribution of nucleotides different than a natural polynucleotide.

CONCLUSION

The terms "a," "an," "the" and similar referents used in the context of describing the invention (especially in the context of the following claims) are to be construed to cover both the singular and the plural, unless otherwise indicated herein or clearly contradicted by context. The term "based on" is to be construed to cover both exclusive and nonexclusive relationships. For example, "A is based on B" means that A is based at least in part on B and may be based wholly on B. By "about" is meant a quantity, amount, level, value, number, frequency, percentage, dimension, size, weight, or length that varies by as much as 10, 9, 8, 7, 6, 5, 4, 3, 2, or 1% to a reference quantity, amount, level, value, number, frequency, percentage, dimension, size, weight, or length.

All methods described herein can be performed in any suitable order unless otherwise indicated herein or otherwise clearly contradicted by context. The use of all examples and exemplary language (e.g., "such as" or "for example") provided herein is intended merely to better illuminate aspects of the invention and do not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified, thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

Furthermore, references have been made to publications, patents and/or patent applications (collectively "references") throughout this specification. Each of the cited references is individually incorporated herein by reference for their particular cited teachings as well as for all that they disclose.

The invention claimed is:

1. A method for sequencing a polynucleotide strand comprising:
  receiving at least 10,000 polynucleotide strands having a distribution of nucleotides at a polynucleotide sequencer;
  receiving metadata describing the distribution of nucleotides in the polynucleotide strands;
  modifying a base-calling algorithm that processes raw data from the polynucleotide sequencer representing the at least 10,000 polynucleotide strands, the modifying based on the metadata to create a modified base-calling algorithm, wherein:
    the metadata comprises an indication of a high-diversity region of the polynucleotide strand and the modified base-calling algorithm uses reads from the high-diversity region for calibration of base calling;
    the metadata comprises an indication of a partial sequence of the polynucleotide strand and the modified base-calling algorithm is limited to making base calls over a region of the polynucleotide strand that match the partial sequence;
    the metadata comprises a list of nucleotide bases present in the polynucleotide strand and the modified base-calling algorithm makes base calls from the list;
    the metadata comprises at least one of analysis direction of the polynucleotide strand, information density of the polynucleotide strand, a precision standard for the polynucleotide strand, or a length of the polynucleotide strand; or
    the metadata comprises an indication that homopolymers are absent and the modified base-calling algorithm does not call homopolymers; and
  generating polynucleotide sequence data from the polynucleotide strands based on the modified base-calling algorithm.

2. The method of claim 1, wherein the polynucleotide strands include a polynucleotide strand beginning and ending with primer binding regions and including a payload region in the middle that encodes binary data.

3. The method of claim 1, wherein the base-calling algorithm calls individual bases using a model in which each individual base has a probability between about 22 to 28% of being adenine (A), between about 22 to 28% of being guanine (G), between about 22 to 28% of being cytosine (C), and between about 22 to 28% of being thymine (T) and the modified base-calling algorithm calls individual bases using a model in which each individual base has a greater than 15% difference in probability of being one of A, G, C, or T.

4. A polynucleotide sequencer system comprising:
a sensor configured to generate a signal indicative of a nucleotide base associated with a sensed polynucleotide;
computer-readable media comprising instructions that when executed by a processor cause the processor to:
receive data describing a characteristic of at least 10,000 sensed polynucleotides;
generate a custom base-calling algorithm that processes the signal generated by the sensor of the polynucleotide sequencer system representing the at least 10,000 sensed polynucleotides, the generation based on a default base-calling algorithm and the characteristic of the sensed polynucleotide provided to the polynucleotide sequencer system, wherein the default base-calling algorithm calls individual bases using a model in which each individual base has a probability between about 22 to 28% of being adenine (A), between about 22 to 28% of being guanine (G), between about 22 to 28% of being cytosine (C), and between about 22 to 28% of being thymine (T) and the custom base-calling algorithm calls individual bases using a model in which each individual base has a greater than 15% difference in probability of being one of A, G, C, or T; and
create sequence data based on the characteristics of the signal and the custom base-calling algorithm; and
an output device configured to render the sequence data in a human-readable form.

5. The polynucleotide sequencer system of claim 4, wherein the sensor comprises a camera and the signal comprises a color detected by the camera.

6. The polynucleotide sequencer system of claim 4, wherein the sensor comprises an electrically resistant membrane having a nanopore and the signal comprises an electrical current.

7. The polynucleotide sequencer system of claim 4, wherein the characteristic is absence of homopolymers, the default base-calling algorithm interprets the signal so that a homopolymer is called, and the custom base-calling algorithm interprets the signal so that homopolymers are not called.

8. The polynucleotide sequencer system of claim 4, wherein the signal as interpreted by the default base-calling algorithm is associated with a first set of probabilities corresponding to standard nucleotide bases and the custom base-calling algorithm uses a second set of probabilities that are based on the characteristic of the sensed polynucleotides.

9. The polynucleotide sequencer system of claim 4, wherein the characteristic comprises at least one of a base order probability, a list of nucleotide bases present in the sensed polynucleotides, a length of the sensed polynucleotides, or a layout of the sensed polynucleotides.

10. A method for correcting sequencing data based on a characteristic of polynucleotide strands, the method comprising;
generating first sequence data for at least 10,000 polynucleotide strands according to a first base-calling algorithm;
receiving data describing a characteristic of the polynucleotide strands;
comparing the first sequence data to the characteristic of the polynucleotide strands;
identifying a difference between the first sequence data and the characteristic;
modifying the first base-calling algorithm based on the difference to create a second base-calling algorithm or accessing a pre-existing third base-calling algorithm identified based on the difference; and
generating second sequence data for the polynucleotide strands according to the second base-calling algorithm or the third base-calling algorithm.

11. The method of claim 10, wherein the difference comprises a base call in the first sequence data that differs from the characteristic of the polynucleotide strands.

12. The method of claim 10, wherein the difference comprises a frequency of a nucleotide base and modifying the first base-calling algorithm comprises changing a probability associated with the nucleotide base being included in the polynucleotide strands.

13. The method of claim 10, wherein the difference comprises region-specific nucleotide diversity and modifying the first base-calling algorithm comprises assigning a correspondence between at least two regions of a polynucleotide strand included in the polynucleotide strands and at least two corresponding target nucleotide diversities.

14. The method of claim 13, wherein a first region of the at least two regions corresponds to a primer binding site and is assigned a diversity indicating that at least about 95% of all the polynucleotide strands include a same nucleotide base at positions in the first region, and a second region of the at least two regions corresponds to a payload region and is assigned a diversity indicating that of all the polynucleotide strands there is an about equal distribution of nucleotide bases at positions in the second region.

15. The method of claim 10, wherein the difference comprises presence of a nucleotide base in the first sequence data that, based on the characteristic, is not present in the polynucleotide strands or absence of a synthetic nucleotide base in the first sequence data that, based on the characteristic, is present in the polynucleotide strands.

16. The method of claim 10, wherein the characteristic comprises strand length, the difference comprises a difference in strand length, and modifying the first-base calling algorithm comprises modifying a phasing of the first base-calling algorithm.

17. The method of claim 10, wherein the polynucleotide strands have a distribution of nucleotides different than genomic DNA with respect to at least one of a frequency of individual nucleotide bases, a number of types of individual nucleotide bases, or an ordering of nucleotide bases.

* * * * *